(12) United States Patent
Canonaco et al.

(10) Patent No.: US 8,435,247 B2
(45) Date of Patent: May 7, 2013

(54) LINKED TIBIAL RESECTION GUIDE

(75) Inventors: Alex F. Canonaco, Caldwell, NJ (US); Sandeep K. Chauhan, Plumpton Green (GB)

(73) Assignee: Howmedica Osteonics Corp., Mahwah, NJ (US)

( * ) Notice: Subject to any disclaimer, the term of this patent is extended or adjusted under 35 U.S.C. 154(b) by 100 days.

(21) Appl. No.: 12/861,973

(22) Filed: Aug. 24, 2010

(65) Prior Publication Data

US 2010/0318090 A1 Dec. 16, 2010

Related U.S. Application Data

(62) Division of application No. 11/698,761, filed on Jan. 26, 2007, now abandoned.

(51) Int. Cl.
*A61B 17/58* (2006.01)
*A61B 17/60* (2006.01)
*A61F 2/00* (2006.01)

(52) U.S. Cl.
USPC .......................................................... 606/88

(58) Field of Classification Search ............... 606/87–89
See application file for complete search history.

(56) References Cited

U.S. PATENT DOCUMENTS

| | | |
|---|---|---|
| 329,149 A | 10/1885 | Eager |
| 4,309,778 A | 1/1982 | Buechel et al. |
| 5,234,433 A | 8/1993 | Bert et al. |
| 5,364,402 A | 11/1994 | Mumme et al. |
| 5,611,802 A | 3/1997 | Samuelson et al. |
| 5,624,444 A | 4/1997 | Wixon et al. |
| 5,782,925 A | 7/1998 | Collazo et al. |
| 5,885,284 A | 3/1999 | Errico et al. |
| 6,013,081 A | 1/2000 | Burkinshaw et al. |
| 6,024,746 A | 2/2000 | Katz |
| 6,482,209 B1 * | 11/2002 | Engh et al. ..................... 606/79 |
| 6,554,838 B2 | 4/2003 | McGovern et al. |
| 7,083,624 B2 | 8/2006 | Irving |
| 7,201,755 B2 | 4/2007 | Faoro et al. |
| 7,601,154 B2 | 10/2009 | Kuczynski et al. |
| 2003/0100906 A1 | 5/2003 | Rosa et al. |
| 2003/0130665 A1 | 7/2003 | Pinczewski et al. |
| 2003/0171757 A1 | 9/2003 | Coon et al. |
| 2005/0149040 A1* | 7/2005 | Haines et al. ................... 606/88 |
| 2005/0171545 A1 | 8/2005 | Walsh et al. |
| 2005/0192588 A1 | 9/2005 | Garcia |
| 2005/0261697 A1 | 11/2005 | Canonaco et al. |
| 2006/0142774 A1 | 6/2006 | Metzger |
| 2006/0276796 A1 | 12/2006 | Creger et al. |
| 2006/0293682 A1 | 12/2006 | Justin et al. |
| 2007/0288029 A1 | 12/2007 | Justin et al. |

OTHER PUBLICATIONS

Freeman, Biomet: Total Knee Replacement System, published 1985, 56 pages.
Protek F/S Modular Total Knee Replacement System, pp. 1-57, published by Protek in Jan. 1991.
Proteck Mark II Total Knee Replacement System, 1987, pp. 1-31.

* cited by examiner

*Primary Examiner* — Sameh Boles
(74) *Attorney, Agent, or Firm* — Lerner, David, Littenberg, Krumholz & Mentlik, LLP

(57) ABSTRACT

An improved resection guide and method using same are disclosed. The guide is preferably utilized in resecting the tibia during either a single or double unicondylar type procedure. Preferably, the guide allows for linked resection of the tibia while also being capable of conforming to many different patient sizes. This may also allow for a more precise resection to be accomplished.

17 Claims, 14 Drawing Sheets

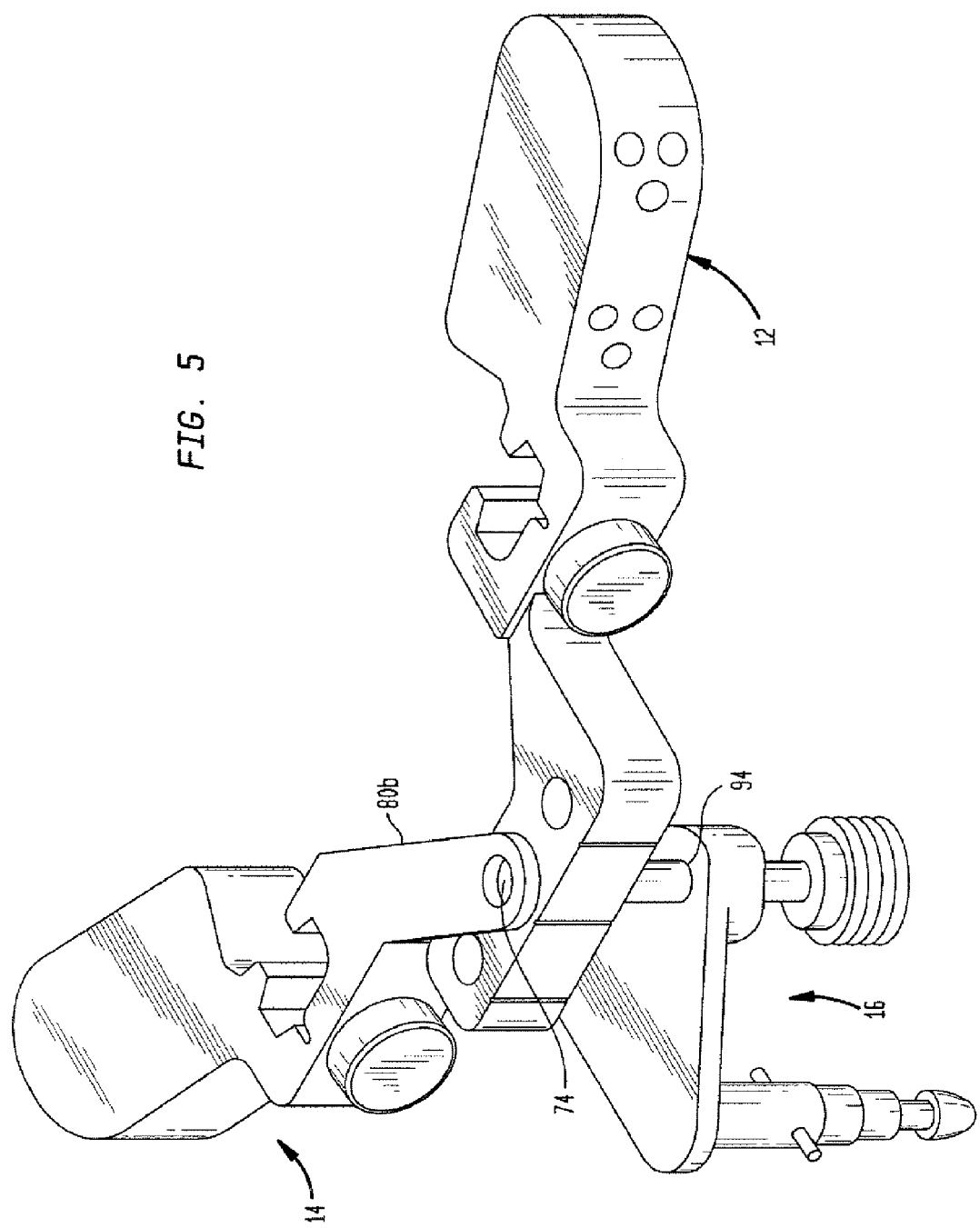

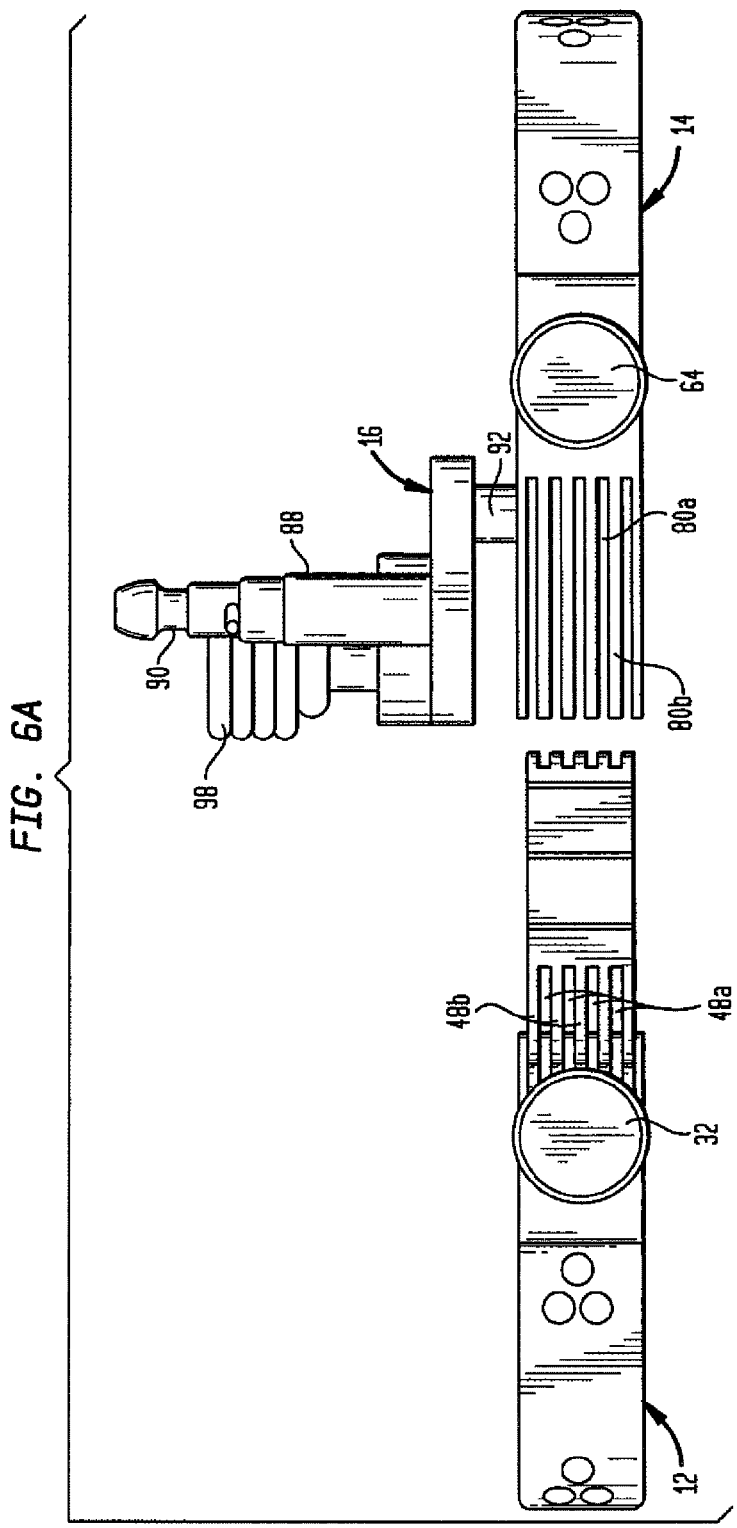

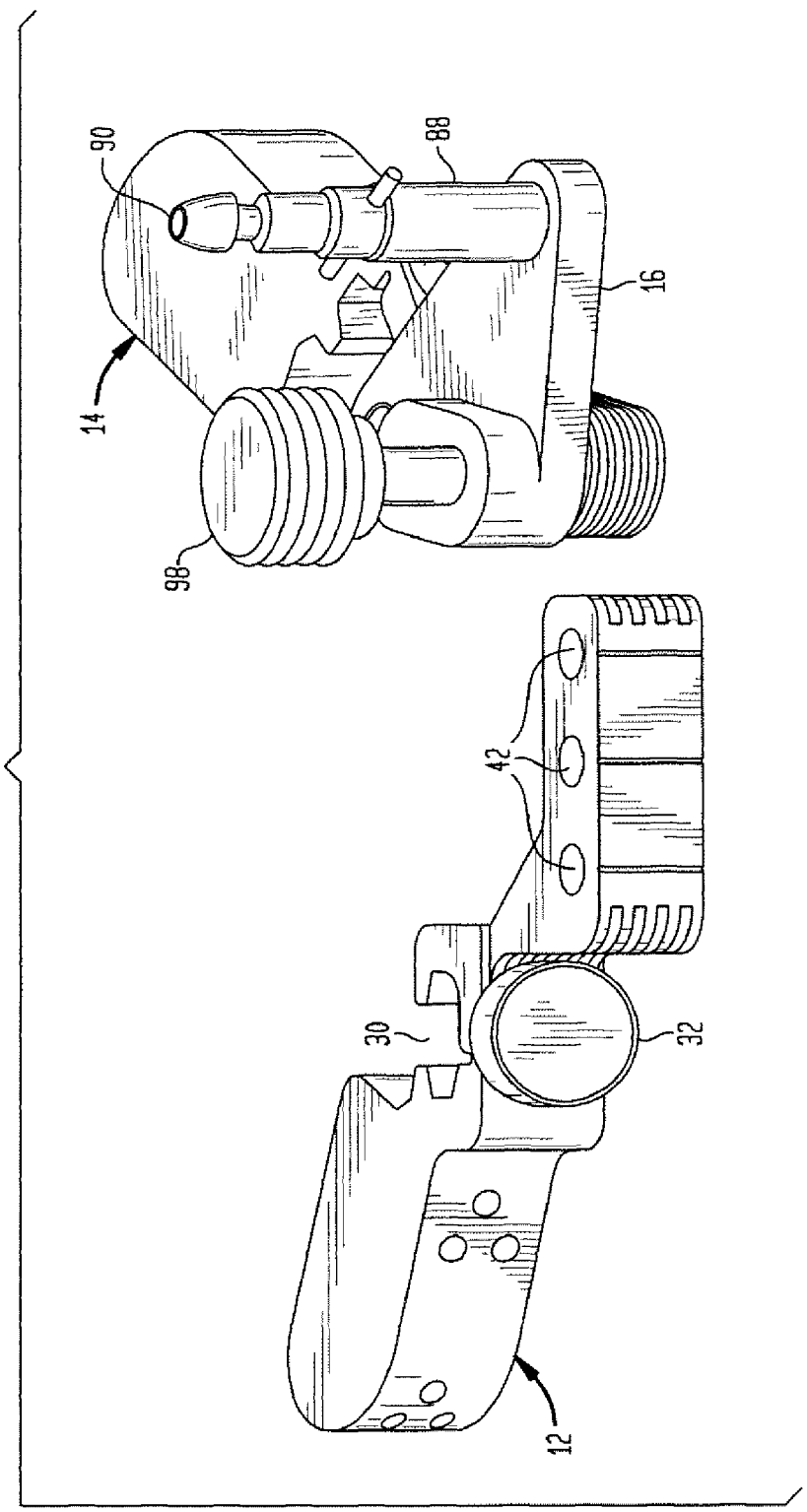

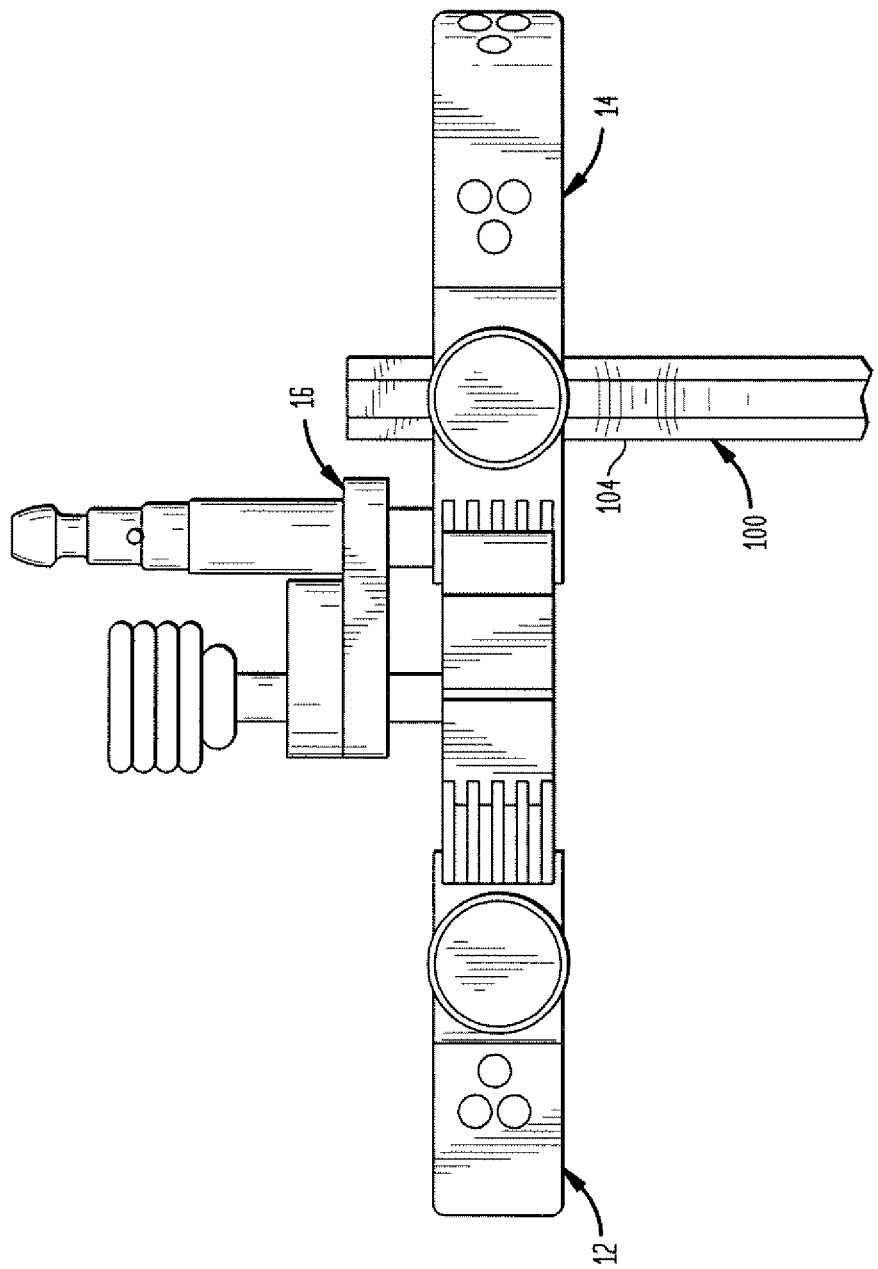

LINKED TIBIAL RESECTION GUIDE

CROSS-REFERENCE TO RELATED APPLICATIONS

This application is a divisional of U.S. application Ser. No. 11/698,761, filed on Jan. 26, 2007, the disclosure of which is incorporated herein by reference.

BACKGROUND OF THE INVENTION

The field of orthopedic surgery is a constantly evolving one. While the same anatomical problems often occur in patients and require orthopedic procedures, the apparatus and methods for performing the many different surgeries often change. Surgeons must keep up with the latest and greatest technology in order to continue to better serve their patients. For instance, there exist many different procedures for alleviating pain in, restoring normal movement to, and otherwise repairing the knee joint. Whether traditional or minimally invasive, or full or partial, knee replacement surgery has become a common orthopedic procedure. The present invention relates to an improved apparatus utilized in an improved method for performing one or two simultaneous unicondylar knee replacement procedure(s).

A unicondylar procedure typically involves the replacement of only one compartment of the knee joint, rather than the entire joint. Specifically, a unicondylar procedure generally involves replacement of portions of either the medial or lateral compartments of the knee joint. For example, in certain patients the surfaces of the proximal tibia and distal femur will only be worn on either the medial or lateral side. This is often due to injury or wear caused by a certain activity or movement (e.g., running, walking, etc . . . ). A unicondylar procedure will see the damaged articulation surfaces (on both the tibia and femur) of the affected compartment being resected and replaced with artificial implants that essentially recreate the surfaces and allow for the needed articulation in the joint. Typically, this procedure is performed through a single incision located in the skin on either the anterior aspect or side aspect, adjacent the affected compartment of the knee joint. This type of procedure is a widely utilized technique for accomplishing the restoration of normal operation to a damaged knee joint and alleviation of pain in a patient.

Recently, it has become common place to perform two of the aforementioned unicondylar replacement procedures in lieu of a total knee replacement procedure. Instead of resecting the entire surfaces of the proximal tibia and distal femur, as is often done in a total replacement procedure, utilizing two unicondylar procedures to replace both the medial and lateral compartments allows for some of the bone surfaces to remain in place and certain of the ligaments and tendons in the knee to remain intact (e.g., the ACL). However, performing a procedure in this fashion poses certain difficulties to a surgeon. For example, each of the resections of the either the tibia or femur must done so that the medial and lateral aspects of each bone are linked so as to allow proper balancing of the joint upon implantation of replacement implants. Thus, instruments have been created which allow for linked resections to be made on either the tibia or femur. Nonetheless, these instruments have their own drawbacks, such as their inability to conform to differently sized patients and their inability to allow precise cutting of the bone.

Therefore, there exists a need for an improved linked resection guide for use in either a single or double unicondylar procedure.

BRIEF SUMMARY OF THE INVENTION

A first aspect of the present invention is a tibial resection guide. The guide includes a first resection guide portion including a first cutting surface and a second resection guide portion including a second cutting surface. The second resection guide portion is preferably pivotally connected to the first resection guide portion, and the first and second cutting surfaces are preferably positioned with respect to one another so as to allow linked cuts to be made on lateral and medial sides of a proximal tibia during a surgical procedure on the knee.

In other embodiments of the first aspect of the present invention the first resection guide portion may include a first channel and the second resection guide portion may include a second channel. The first resection guide portion may also include a first connection aperture and the second resection guide portion may also include a second connection aperture. The tibial resection guide may include a connector pivotally connecting the first and second resection guide portions to one another, the connector extending through the first and second connection apertures. Alternatively, the tibial resection may include an intermediate portion having a first extension, the first extension extending through the first and second connection apertures. The intermediate portion may include a second extension adapted to receive a navigation tracker and an intermediate aperture. The tibial resection guide may include a locking knob extending through the intermediate aperture and the first and second connection apertures. The tibial resection guide may also include a leg extension inserted through one of the first or second channels, where the leg extension includes a main body, a vertically extending rod, and a leg clamp. The vertically extending rod may be held in one of the first or second channels with either a first set screw at least partially extending into the first channel or a second set screw at least partially extending into the second channel. In a preferred embodiment, the tibial resection guide is adapted for use with an oscillating tip saw. The first and second resection guide portions may also each include a fixing aperture.

A second aspect of the present invention is a method of resecting a tibia during a surgical procedure. In accordance with this aspect, the method includes the steps of providing a tibial resection guide including a first resection guide portion including a first cutting surface and a second resection guide portion including a second cutting surface, the second resection guide portion being pivotally connected to the first resection guide portion, vertically positioning the tibial resection guide with respect to a portion of the tibia to be resected, rotating one of the first or second resection guide portions with respect to the other in order to position the first and second cutting surfaces with respect to the portion of the tibia to be resected, engaging a portion of a cutting instrument with one or both of the first and second cutting surfaces, and resecting the portion of the tibia.

In other embodiments of this second aspect, the method may also include the steps of fixing the first and second resection guide portions with respect to the tibia, the step of fixing the first and second resection guide portions with respect to one another, or the step of fixing one of the first or second resection guide portions to a leg extension. The vertically positioning step may include sliding a vertically extending rod of the leg extension through a first channel formed in the first resection guide portion or through a second channel formed in the second resection guide portion. Likewise, the engaging and resecting steps are performed with an oscillating tip saw. In any of the mentioned methods, both medial and lateral sides of the tibia may be resected, or just one of such may be resected.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 5 is a bottom perspective view of the tibial resection guide of FIG. 1.

FIGS. 6A and 6B are exploded views of the tibial resection guide of FIG. 1.

FIG. 7 is a perspective view of the tibial resection guide of FIG. 1, in conjunction with a portion of a leg attachment.

DETAILED DESCRIPTION

Figure 1:
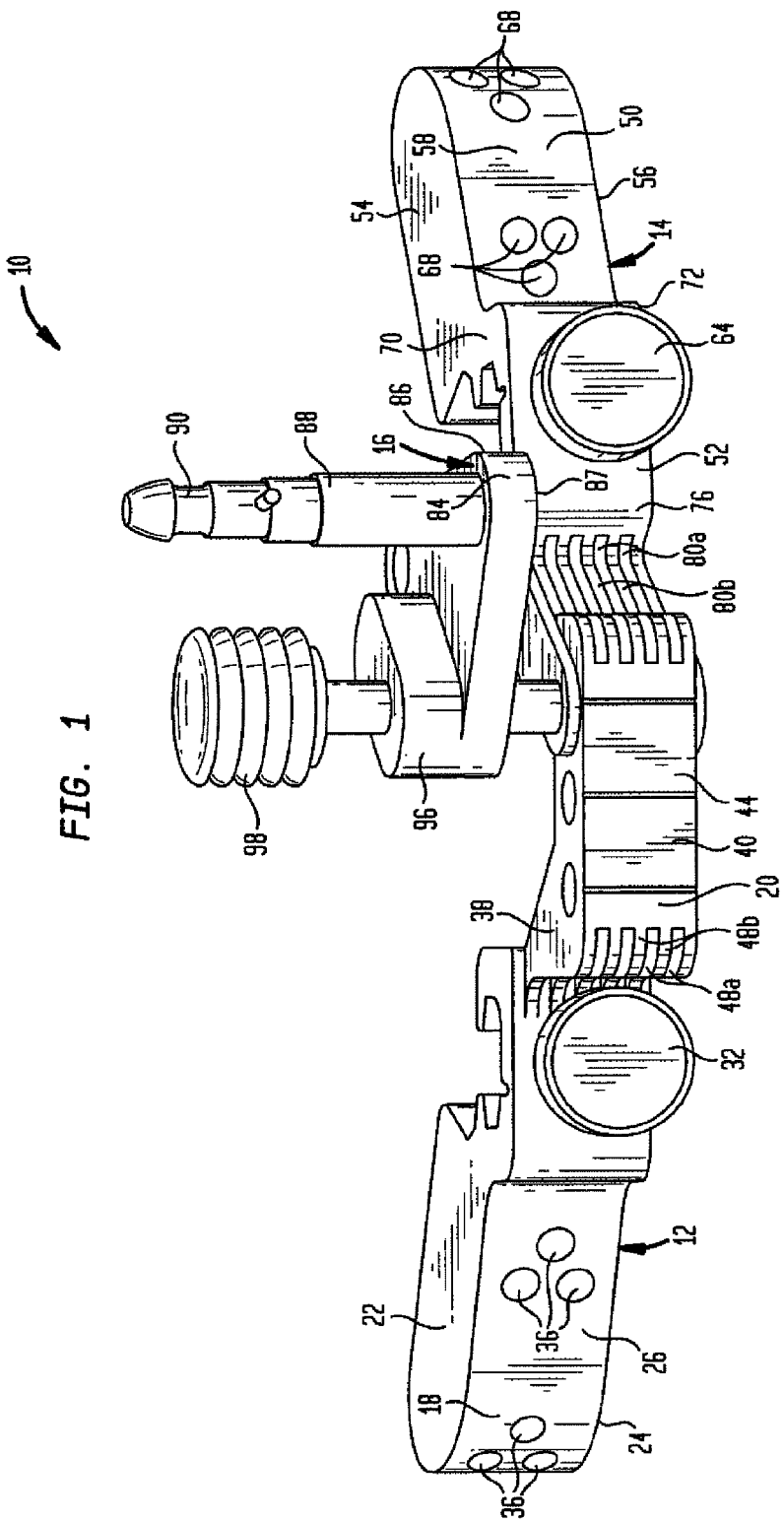
FIG. 1 is a front perspective view of a tibial resection guide in accordance with an embodiment of the present invention.
Figure 2:
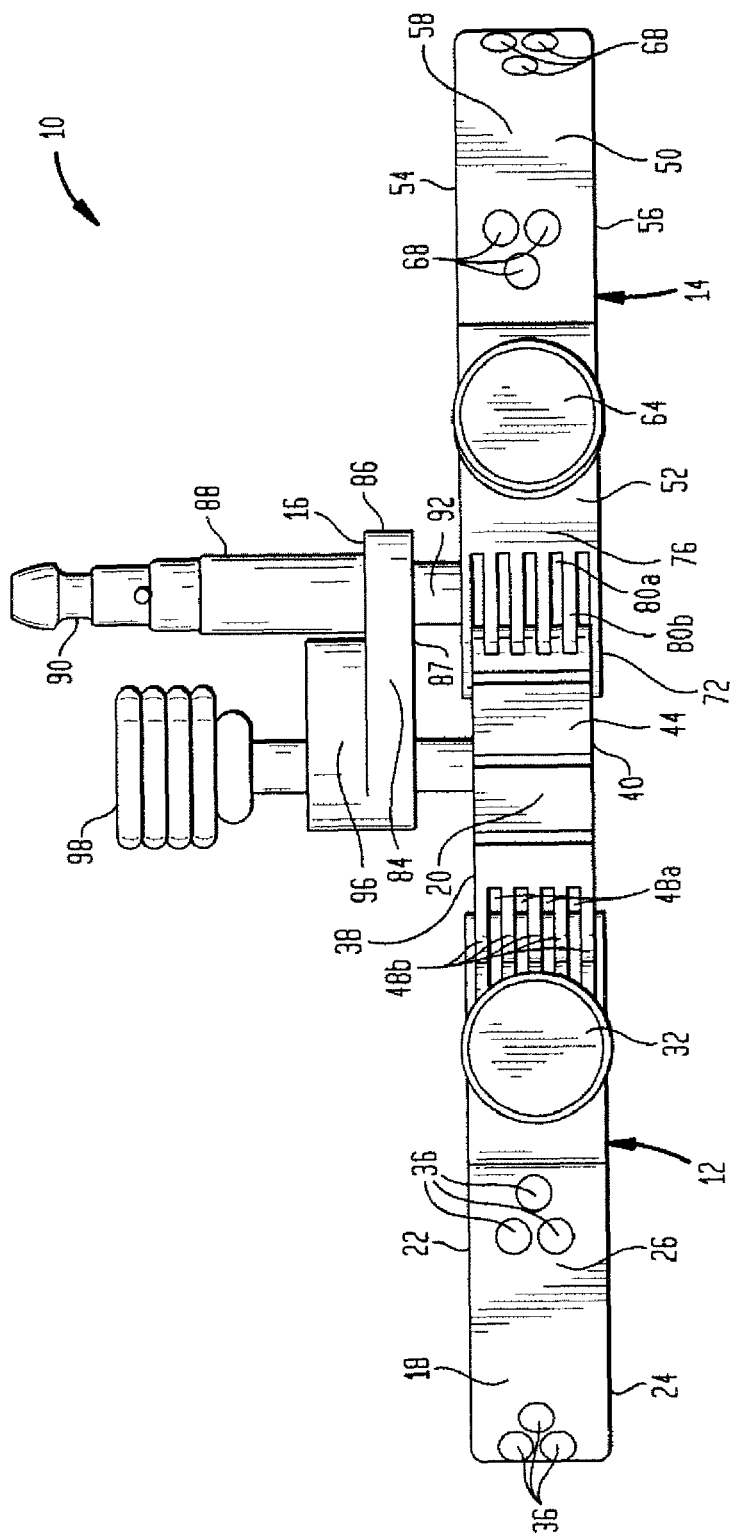
FIG. 2 is a front view of the tibial resection guide of FIG. 1.
Figure 3:
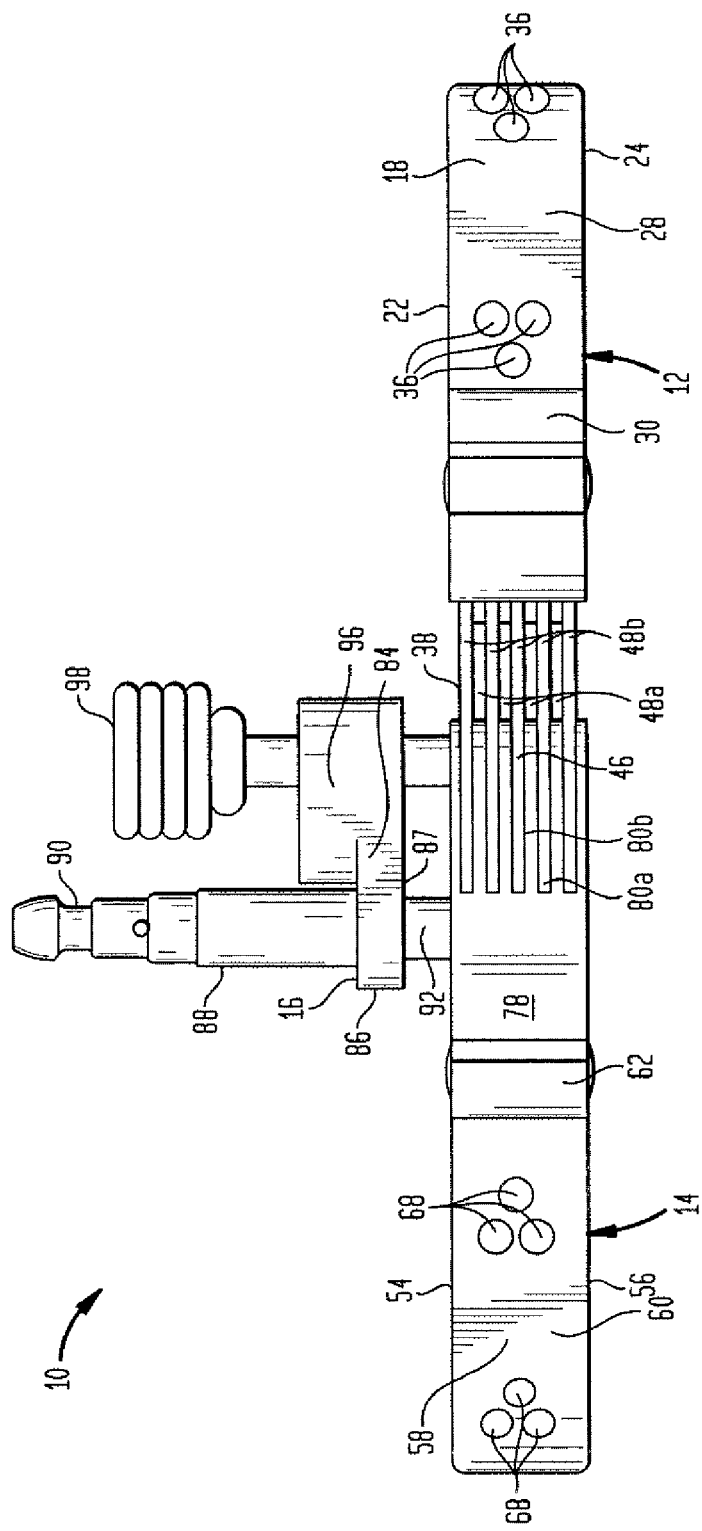
FIG. 3 is a rear view of the tibial resection guide of FIG. 1.
Figure 4:
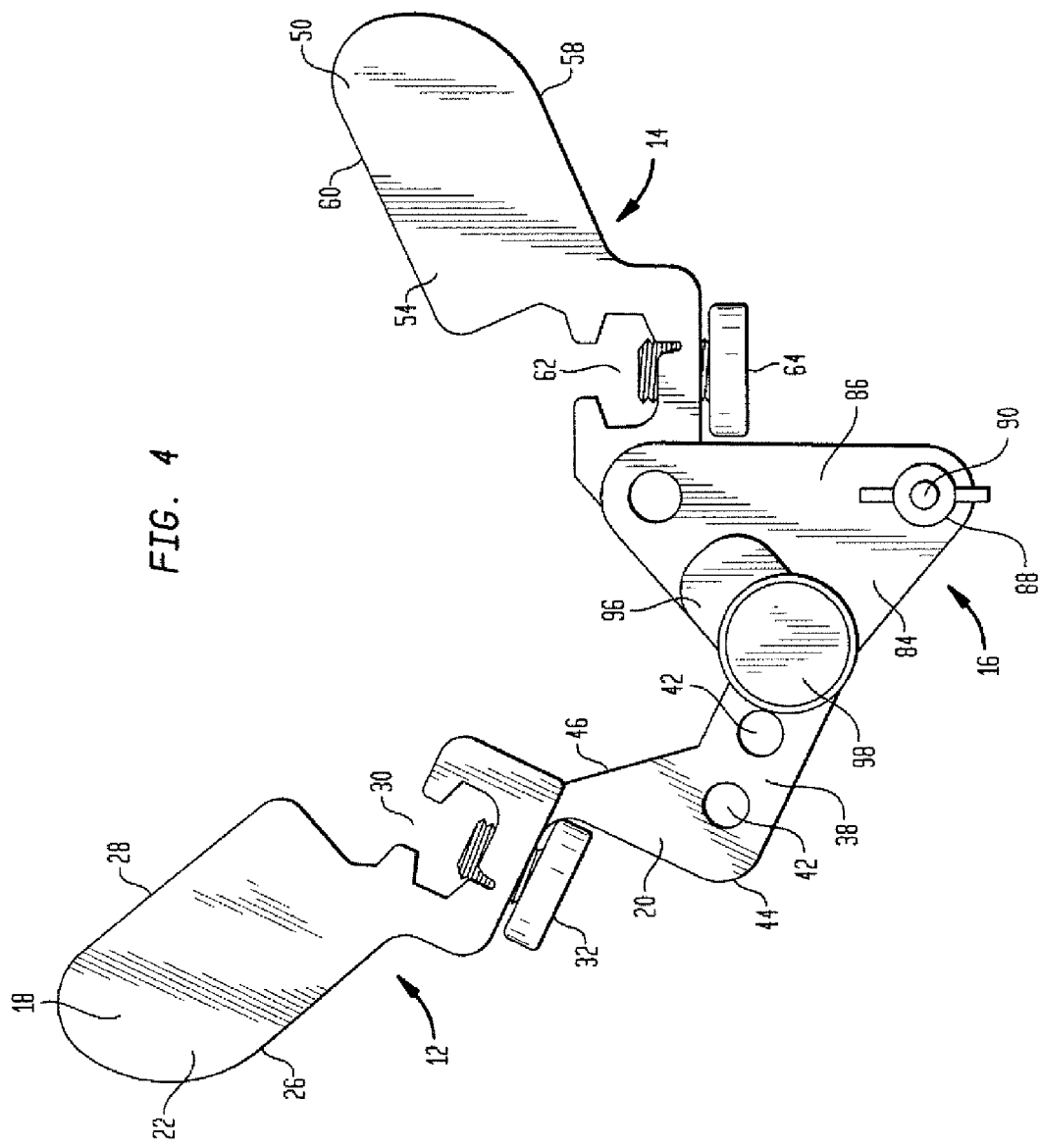
FIG. 4 is a top view of the tibial resection guide of FIG. 1.

Referring to the drawings, wherein like reference numerals refer to like elements, FIGS. 1-10 depict a first embodiment resection guide, designated generally by reference numeral 10. In the embodiment shown, guide 10 is configured for use in resecting the tibia during a single or double unicondylar procedure. However, it is to be understood that certain of the novel aspects of guide 10 could be employed in other guides designed for resection of different bones during the same or different procedures. Guide 10 includes three main components which enable it to operate in the fashion discussed herein, a first resection guide portion 12, a second resection guide portion 14, and an intermediate portion 16. Each of these components, and the method of utilizing guide 10, will be discussed more fully below.

First guide portion 12 includes a first body 18 and a second body 20. First body 18 further includes a top surface 22, a bottom surface 24, a front face 26 and a rear face 28 (best shown in FIG. 3). In addition, first body 18 defines a channel 30 (best shown in FIG. 4) extending from top surface 22 to bottom surface 24 near where first body 18 connects with second body 20. A set screw 32 preferably extends through a threaded aperture 34 from front face 26 toward rear face 28, and into channel 30. Rotation of set screw 32 in one direction or the other acts so as to move a portion of the screw into or out of channel 30. First body 18 also includes one or more fixing apertures 36 extending from front face 26 to rear face 28. These apertures are preferably designed to receive pins or the like to facilitate a reinforcing connection of guide portion 12 to a bone, such as the tibia.

Second body 20 of first guide portion 12 is preferably connected to first body 18. Second body 20 includes its own top surface 38 and bottom surface 40, and one or more connection apertures 42 (best shown in FIG. 4) extending through body 20 from the top to bottom surfaces. In addition, second body 20 includes a front face 44 and a rear face 46 (best shown in FIG. 3), and may include one or more elongate apertures 48a extending through at least a portion of body 20 from the front face to the rear face, or partially therethrough, which create a series of fingers 48b. In the embodiment shown, second body 20 may be formed integrally with first body 18 through, for example a molding or milling process, or body 20 may be fixably attached to body 18 through the use of, for example, a welding or other well-known attachment process. In certain embodiments, it is possible for second body 20 to be moveable with respect to first body 18.

Second guide portion 14 includes several elements similar to those of first guide portion 12. More particularly, second guide portion 14 includes a first body 50 and a second body 52. First body 50 further includes a top surface 54, a bottom surface 56, a front face 58 and a rear face 60 (best shown in FIG. 3). In addition, first body 50 defines a channel 62 (best shown in FIG. 4) extending from top surface 54 to bottom surface 56 near where first body 50 connects with second body 52. A set screw 64 preferably extends through a threaded aperture 66 from front face 58 toward rear face 60, and into channel 62. Rotation of set screw 64 in one direction or the other acts so as to move a portion of the screw into or out of channel 62. First body 50 also includes one or more fixing apertures 68 extending from front face 50 to rear face 60. These apertures are preferably designed to receive pins or the like to facilitate a reinforcing connection of guide portion 14 to a bone, such as the tibia.

Second body 52 of second guide portion 14 is preferably connected to first body 50. Second body 52 includes its own top surface 70 and bottom surface 72, and one or more connection apertures 74 (best shown in FIG. 5) extending through body 52 from the top to bottom surfaces. In addition, second body 52 includes a front face 76 and a rear face 78 (best shown in FIG. 3), and may include one or more elongate apertures 80a extending through at least a portion of body 52 from the front face to the rear face, or partially therethrough, which create a series of fingers 80b. As with guide portion 12, second body 52 may be formed integrally with first body 50 through, for example a molding or milling process, or body 52 may be fixable attached to body 50 through the use of, for example, a welding or other well-known attachment process. Once again, in certain embodiments, it is possible for second body 52 to be moveable with respect to first body 50.

Intermediate portion 16 is made up in large part by a triangular-shaped body 84 having a top surface 86 and a bottom surface 87. A first extension 88 preferably extends from top surface 86 and includes a connector 90. A second extension 92 preferably extends from bottom surface 87. Finally, body 84 includes at least one aperture 94 (best shown in FIG. 5) extending from top surface 86 to bottom surface 87. Aperture 94 may also extend through a shoulder 96 which extends from top surface 86 and upward, as is shown in the figures. While body 84 is shown as a triangular shaped body, and such may indeed provide benefits for use in accordance with the present invention, it is to be understood that body 84 could be any shape. Intermediate portion 16 is preferably designed so that second extension 92 extends through one of apertures 74 formed in second body 52 of second guide portion 14, while aperture 94, one of apertures 74 formed in second body 52 of second guide portion 14, and one of apertures 42 formed in second body of first guide portion 12 all align with one another. This alignment preferably allows for a locking knob 98 to be placed through aperture 94, aperture 74 and aperture 42 to form a pivoting connection between first guide portion 12 and second guide portion 14. Thus, first guide portion 12 and second guide portion 14 may rotate with respect to one another. Locking knob 98 is preferably designed so as to lock within shoulder 96 and keep each of the components of guide 10 together and pivotally connected, when desired.

In constructing guide 10, it is noted that the above-discussed elongate apertures 48a, 80a, and fingers 48b, 80b preferably cooperate with one another. As is best shown in FIGS. 3 and 5-6B, such elements preferably align so that the above-discussed pivotal connection may be realized. More particularly, fingers 48b preferably reside within apertures 80a, and fingers 80b preferably reside within apertures 48a, so that an interlaced cooperation of the two portions is formed. This cooperation ensures a solid, yet pivotal fit between portions 12 and 14. Of course, it is to be understood that in other embodiments, different connection configurations may be utilized. For example, more or less fingers/apertures may be employed, one of portion 12 or 14 may include a cut out for receiving a portion of the other portion, or portion 12 and 14 may simply be laid over one another with portions of each aligning with one another. This latter configuration is shown and discussed in relation to a second embodiment discussed below.

Each of the components of guide 10 are preferably constructed of material suitable for use in surgery (e.g., biocompatible materials), and also suitable for use with the cutting apparatus discussed below. In this regard, it is noted that the components should be made of a relatively hard and durable material, like stainless steel or the like. It is to be understood that the various components of guide 10 may vary from what is shown in the figures. For instance, the components of guide 10 may vary in their particular shape depending upon the particular bone being resected or the manner in which the guide is being utilized. All of these variations fall within the scope of the present invention. In addition, it is to be understood that certain different components may be employed in lieu of those shown. For example, instead of screws 32 and 64, another retaining means may be utilized, such as spring detents or the like. Likewise, each of the components of guide 10 may be manufactured in accordance with well-known processes, such as molding, milling or other processes often employed during the manufacture of medical devices and instruments.

In use, guide 10 is preferably first coupled with a leg extension 100, as is shown in FIG. 7. As is more fully shown in FIG. 12, extension 100 includes a main body 102, a vertically extending rod 104, and a foot clamp 106. Such extensions are known in the art and often employed during similar procedures performed on the knee joint. Rod 104 may be vertically moveable with respect to main body 102 through sliding within a vertical passage 108 formed within a top portion of body 102. Rod 104 may be locked in position by a locking screw 110 or other suitable locking mechanism which extends into passage 108. Likewise, clamp 106 may be moveable, this time horizontally, with respect to main body 102. To facilitate this movement, clamp 106 is provided with a horizontally extending rod 112 that is capable of sliding within a horizontal passage 114 formed within a bottom portion of body 102. Once again, a locking screw 116 or other suitable locking mechanism may be provided to lock clamp 106 in place upon the extension of the screw into passage 114. Finally, clamp 106 itself includes two opposed clamping arms 116 and 118 which are positionable with respect to one another so as to clamp around a lower portion of the leg being operated on. In this regard, arms 116 and 118 should be capable of being fixably clamped around the leg and capable of being released upon completion of the surgery or use of guide 10. Arm 116 may include a first arm portion 116a and a second arm portion 116b which are biased with respect to one another. Similarly, arm 118 includes biased first arm portion 118a and second arm portion 118b. This allows arms 116 and 118 to not only clamp a lower portion of the leg, but also to at least partially wrap around same. In order to facilitate the coupling of guide 10 to leg extension 100, rod 104 is preferably inserted through either channel 30 or channel 62, the latter being shown in FIG. 7. Depending upon which channel 30 or 62 rod 104 is inserted through, the respective guide portion 12 or 14 is clearly fixed with respect to extension 100. Once rod 104 is inserted in a given channel 30 or 62, the corresponding set screw 32 or 64 is tightened to thereby lock guide 10 in place. In this regard, set screw 32 or 64 must be initially unscrewed enough to allow the insertion of rod 104 through the respective channel 30 or 62. Although extension 100 is shown fully in connection with a second embodiment guide 10' (discussed below), such may clearly apply to guide 10.

During a double unicondylar procedure, guide 10 is preferably utilized to make resections of the tibia through two incisions in the region of the knee joint. The first step of the surgery is preferably to make incisions in the anterior portion of the knee joint, so that the proximal portion of the tibia may be accessed. Depending upon the cutting instrument being utilized later in the surgery, the size of the incisions may vary. Preferably, such incisions are made in accordance with well-known medical practices. With the incisions made, guide 10 and leg extension 100 may be placed upon the leg being operated on, so that guide lies adjacent or near the incisions. Clamp 106 is placed around a distal portion of the particular leg so as to at least partially affix guide 10 and extension 100 thereto. During this step of initially placing extension 100 on the leg in question, a navigation tracker (shown in FIGS. 8-10 as element 120) may be used in conjunction with a navigation program to aid in the proper placement of the leg extension. Such devices are well-known and widely utilized in the orthopedic field. One example of such is sold under the name "Stryker Navigation System" by the owner of the present application, Howmedica Osteonics Corp. If a navigation system is in fact utilized, clamp 106 may no longer be required. Thus, use of navigation placement may be done with or without clamp 106.

With leg extension 100 in place, guide 10 may be further positioned by the surgeon or other medical professional in order to properly align its guide portions 12 and 14 with the bone to be resected. This step is illustrated in FIG. 7. Like the placement of leg extension 100, the placement of guide 10 may involve the use of a navigation tracker (shown in FIGS. 8-10 as element 122). Tracker 122 is preferably attached through its coupling with connector 90 of intermediate member 16. Such a connection is known and utilized in many different tooling systems. Tracker 122 is preferably utilized to provide information relating to the position of guide 10. For example, a surgeon may first move guide 10 vertically with respect to extension 100. It is to be understood that the aforementioned step of tightened set screws 32 and 64 may be performed before or after this further positioning of guide 10. Of course, in the case where set screws 32 and 64 have been previously tightened, such would need to be loosened enough to allow the needed sliding of rod 104 through channel 30 or 62 of guide 10.

Figure 8:
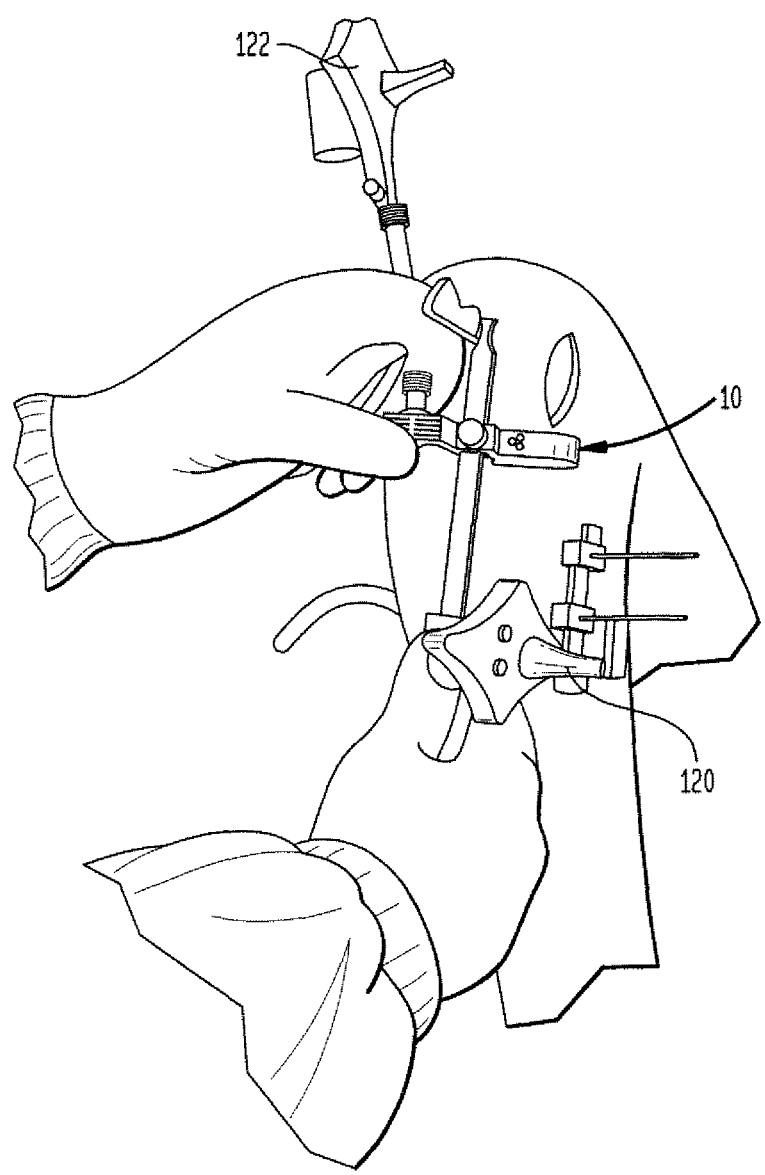
FIG. 8 is a view depicting the placement of the tibial resection guide of FIG. 1 during a surgical procedure.
Figure 9:
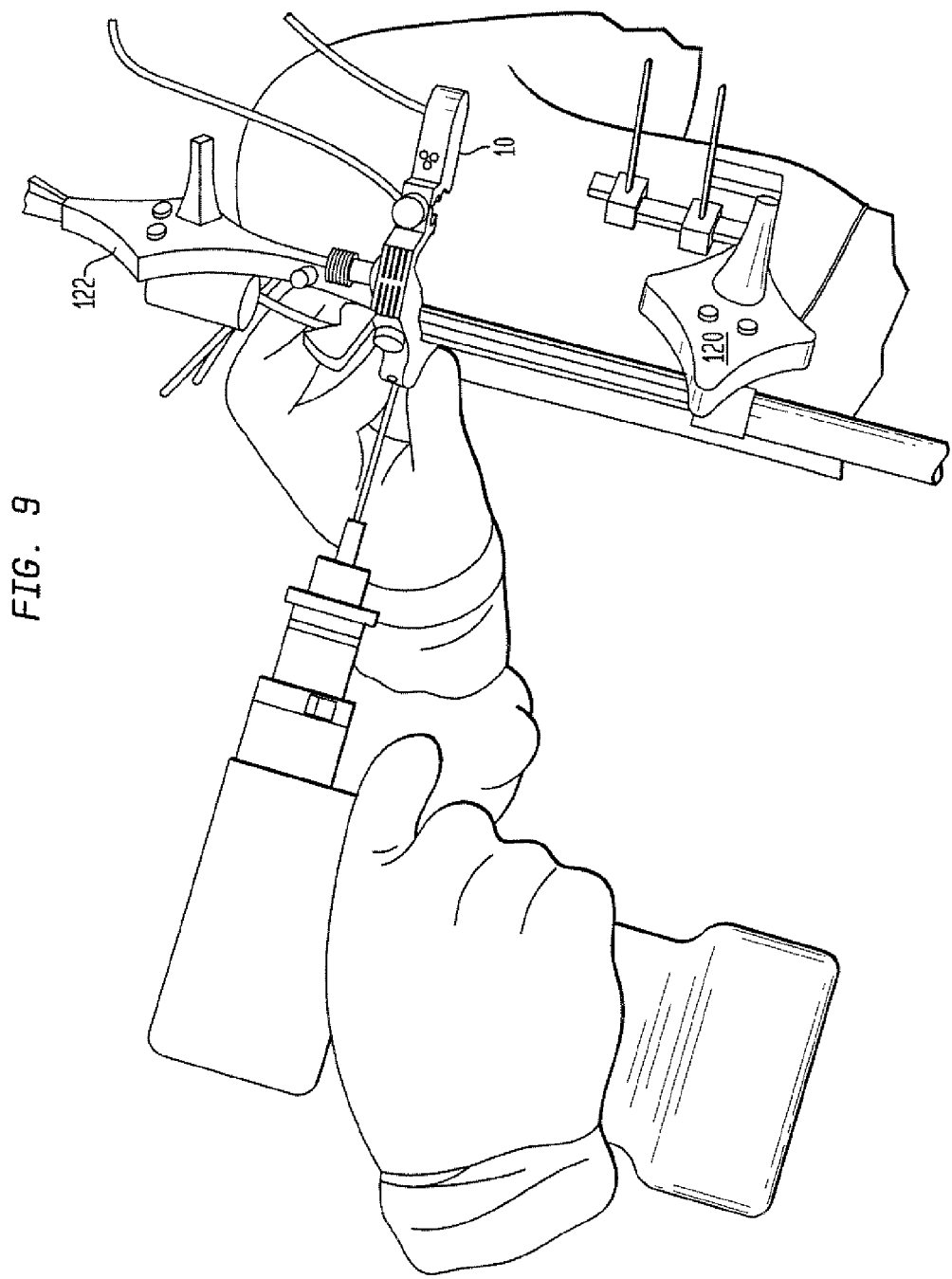
FIG. 9 is a view depicting the insertion of pins through the tibial resection guide of FIG. 1 during a surgical procedure.
Figure 10:
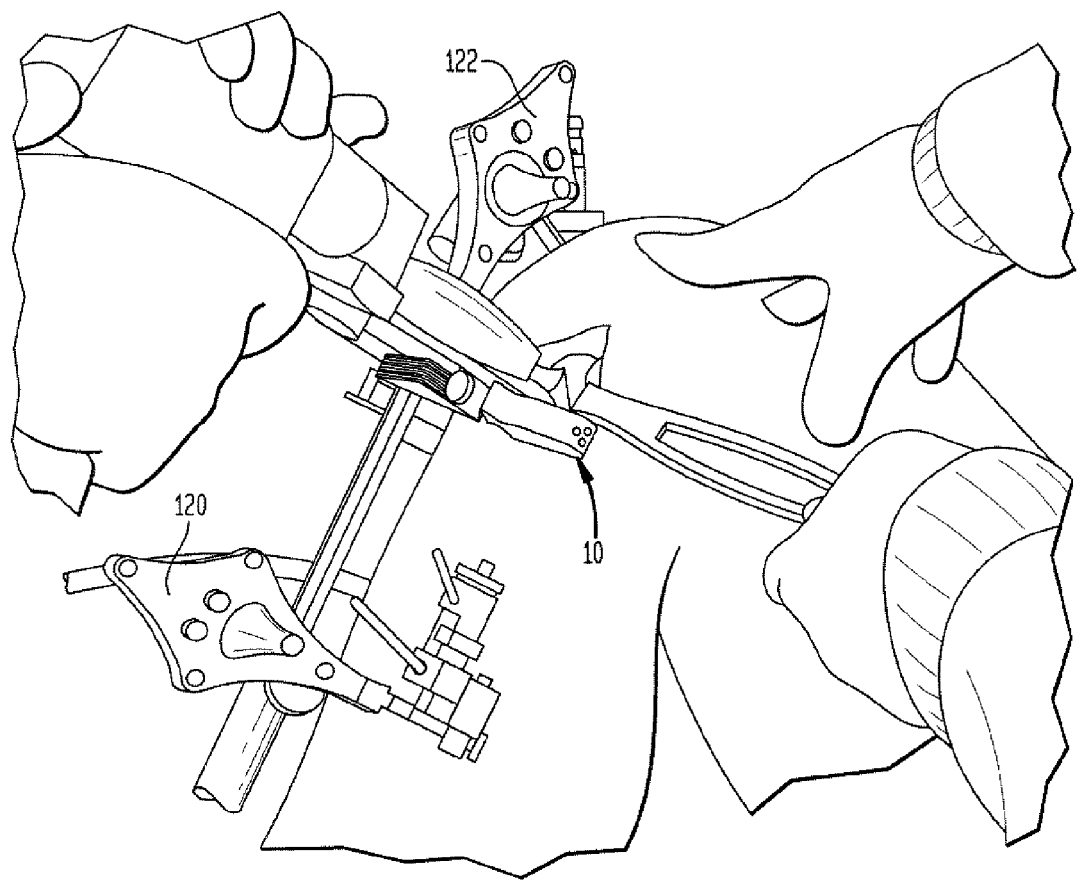
FIG. 10 is a view depicting the cutting of a tibia utilizing the tibial resection guide of FIG. 1 during a surgical procedure.

The positioning step also preferably includes rotating one of guide portions 12 or 14 into position. As is mentioned above, one of guide portions 12 or 14 will be fixed with respect to leg extension 100 depending upon which channel 30 or 62 ultimately accepts rod 104. For example, as is shown in FIGS. 8-10, rod 104 of extension 100 is placed through channel 30 formed in first body 18 of first guide portion 12. During the attachment of leg extension 100, attention should be paid to having first guide portion 12 wind up in its correct position (i.e., with rear face 28 adjacent or touching the skin of the patient at or near the proximal portion of the tibia to be resected). This may involve rotating extension 100 in one direction or the other with respect to the leg. With first guide portion 12 in place, second guide portion 14 may be rotated with respect thereto about the pivot connection formed by locking knob 98 and the cooperation of first guide portion 12, second guide portion 14 and intermediate portion 16 discussed above. It is to be understood that once second guide portion 14 is rotated into position (i.e., with rear face 60 adjacent or touching the skin of the patient at or near the proximal portion of the tibia to be resection), locking knob 98 could be fully tightened to effectively fix portions 12 and 14 with respect to one another.

The cooperation between first guide portion 12, second guide portion 14 and intermediate portion 16 is such that intermediate portion 16 is fixed with respect to one of portions 12 or 14. Thus, the aforementioned rotation step may include rotating one of portion 12 or 14 with respect to the other portion and intermediate portion 16, or rotating one of portion 12 or 14 and intermediate portion 16 with respect to the other portion. However, the inclusion of intermediate portion 16 in guide 10 allows for the overall width of the guide to be varied depending upon the manner which first and second guide portions 12 and 14 are connected with intermediate portion 16. For example, in certain embodiments different apertures of second bodies 20 and 52 may be aligned with one another. Extension 92 of intermediate portion 16 could be inserted through corresponding aligned apertures, as can locking knob 98, in a similar fashion to that described above. Hence, the effective width of guide 10 can be varied depending upon the alignment of first guide portion 12 with respect to second guide portion 14. This provides a guide useful with many differently sized knee joints.

Once guide 10 is placed in the desired position discussed above (preferably confirmed through the use of tracker 122 and to the particular surgeon's liking), the guide may be pinned to the tibia through the utilization of standard bone pins or the like. This is shown in FIG. 9. During this pinning step, the surgeon or other medical professional preferably inserts pins or the like through one or more of apertures 36 and/or 68 located on guide portions 12 and 14, respectively. Most preferably, at least one pin is inserted through at least one of apertures 36 and at least one pin is inserted through at least one of apertures 68. However, any number of pins or other fixing means may be utilized. In this fixed state, it is to be understood that guide portions 12 and 14 of guide 10 are now positioned to allow for the linked resection of both sides of the proximal tibia. In other words, the structure of guide 10, and the method discussed above, allows for certain surfaces of guide 10 to be positioned so as to allow for the correct cuts to be made on both sides of the proximal tibia. Furthermore, the fact that portions 12 and 14 may ultimately be rotated with respect to one another allows the easy positioning of guide 10 for many differently sized patients and knee joints. Similarly, guide 10 may be positioned to ensure more precise cuts for a particular surgeon. For instance, one surgeon may desire guide 10 to be placed as close to the knee joint as possible to better guide his cutting tool, while another surgeon may desire some separation of guide 10 and the knee joint. Guide 10, and more particularly first and second guide portions 12 and 14 may easily be positioned according to the surgeon's liking.

As is best shown in FIG. 10, guide 10 is ultimately used to guide a cutting tool to make the necessary resections on the proximal portion of the tibia. Although many different types of cutting tools may be utilized, an oscillating tip saw is shown in FIG. 10. The particular saw is sold by Stryker Instruments under the name Otis or Stryker Precision Oscillating Tip Saw. Top surfaces 22 and 54 of first and second guide portions 12 and 14 respectively are shown as being used to guide a portion of this saw in cutting the proximal portion of the tibia. It is to be understood that bottom surfaces 24 and 56 of first and second guide portions 12 and 14 respectively could also be utilized in guiding the saw. Of course, the use of the bottom surfaces would require the positioning of guide 10 such that the surfaces properly align with the portion of the proximal tibia to be resected. In other words, guide 10 would most likely need to be moved further vertically should bottom surface 24 and 56 be utilized.

Once the desired cuts are made on the proximal tibia, the remaining steps of the double unicondylar procedure may be performed. This typically involves similarly preparing the distal portion of the femur on both sides, and ultimately placing implants on the various cut surfaces created. These implants preferably replicate the original anatomy and allow for the necessary movement in the knee joint. It is to be understood that guide 10 could also be utilized in making at least certain of the cuts needed in preparing the distal femur. For example, preparation of the distal femur often requires a straight cut, among other cuts. Since this cut is similar to the straight cuts being performed on the proximal tibia, guide 10 could be employed for this step in the surgical procedure also. Of course, guide 10 would preferably need to be repositioned in a similar fashion as is describe above, so that either top surfaces 22 and 54 or bottom surfaces 24 and 56 align with the portion desired to be cut on the distal femur. Alternatively, other guide(s) could be utilized to prepare the distal femur. This would require the removal of at least guide 10, so as to allow the access needed for the surgeon. Once all of the necessary cuts have been made, and the proper implants positioned and affixed, the surgeon may complete the surgery by closing the incisions.

Figure 11:
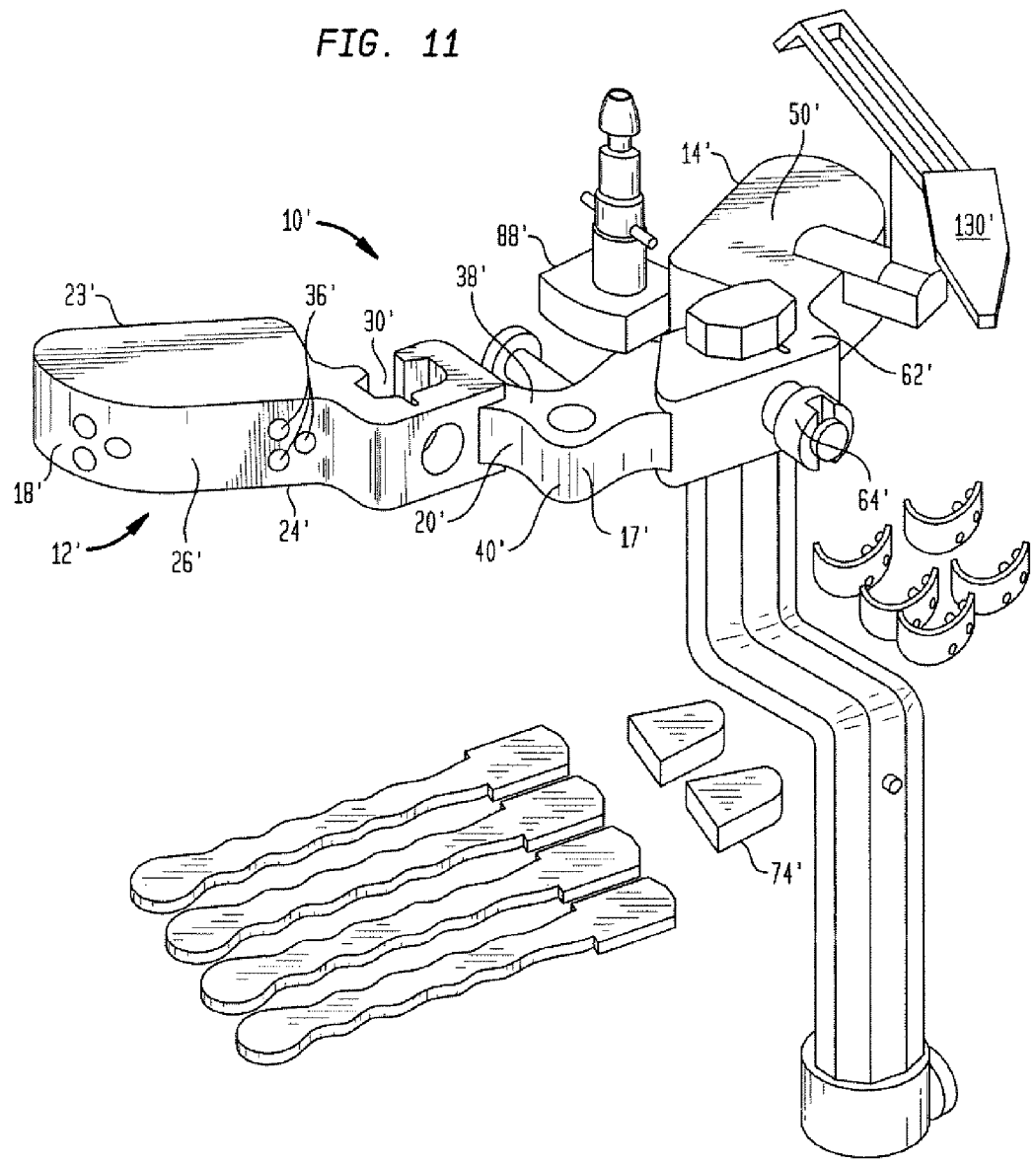
FIG. 11 is a perspective view of a tibial resection guide in accordance with another embodiment of the present invention.
Figure 12:
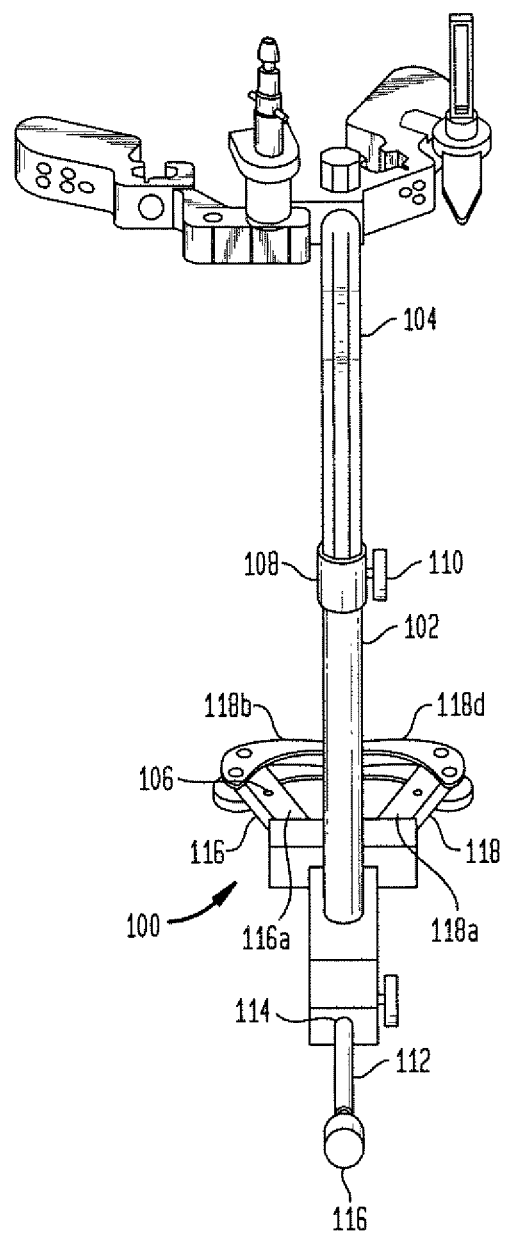
FIG. 12 is a front perspective view of the tibial resection guide of FIG. 10, in conjunction with a leg attachment.
Figure 13:
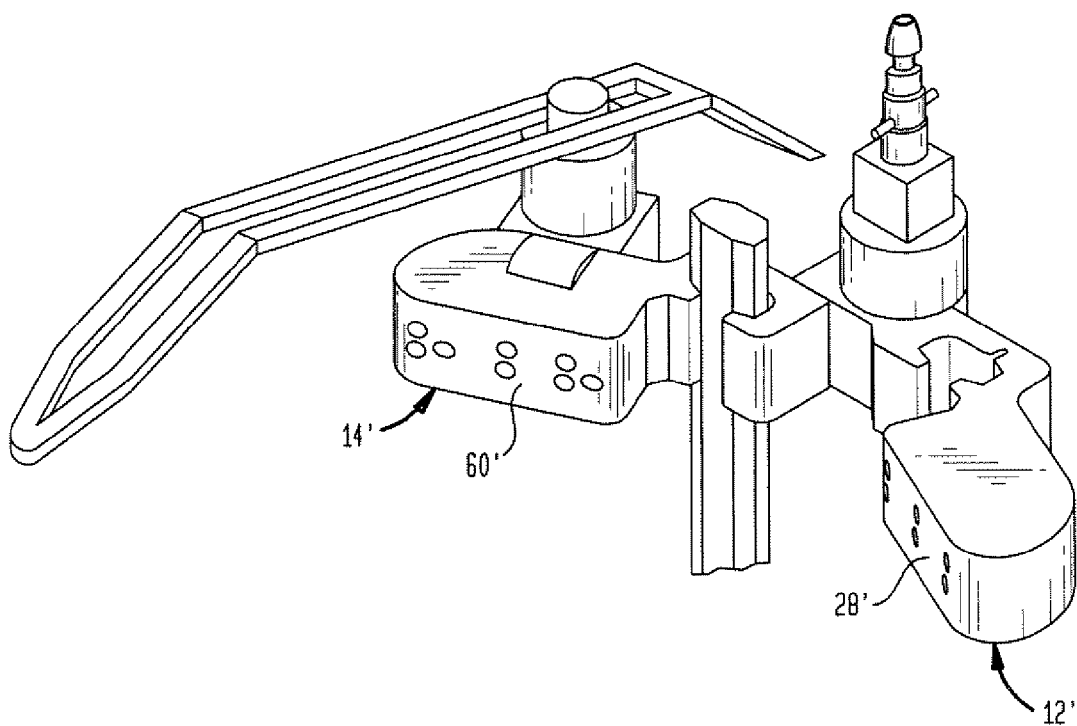
FIG. 13 is a rear perspective view of the tibial resection guide of FIG. 10, in conjunction with a leg attachment.

FIGS. 11-13 depict another embodiment tibial resection guide, designated generally by reference numeral 10'. In fact, because of the similarities between guide 10 and guide 10', like elements of guide 10' have been labeled with similar references numerals to that of guide 10 with a prime indicator. More particularly, guide 10' includes two main components which enable it to operate in a fashion nearly identical to that of guide 10, a first resection guide portion 12' and a second resection guide portion 14'. Each of these components will be discussed more fully below.

First guide portion 12' includes a first body 18' and a second body 20'. First body 18' further includes a top surface 22', a bottom surface 24', a front face 26' and a rear face 28'. In addition, first body 18' defines a channel 30' extending from top surface 22' to bottom surface 24' near where first body 18' connects with second body 20'. A set screw 32' (not shown) preferably extends through a threaded aperture 34' from front face 26' toward rear face 28', and into channel 30'. Rotation of set screw 32' in one direction or the other acts so as to move a portion of the screw into or out of channel 30'. First body 18' also includes one or more fixing apertures 36' extending from front face 26' to rear face 28'. These apertures are preferably designed to receive pins or the like to facilitate a reinforcing connection of guide portion 12' to a bone, such as the tibia.

Second body 20' of first guide portion 12' is preferably connected to first body 18'. Second body 20' includes its own top surface 38' and bottom surface 40', and one or more connection apertures 42' extending through body 20' from the top to bottom surfaces. In addition, second body 20' includes a front face 44' and a rear face 46'. In the second embodiment, second body 20' may be formed integrally with first body 18' through, for example a molding or milling process, or body 20' may be fixable attached to body 18' through the use of, for example, a welding or other well-known attachment process. In certain embodiments, it is possible for second body 20' to be moveable with respect to first body 18'.

Second guide portion 14' includes several elements similar to those of first guide portion 12'. More particularly, second guide portion 14' includes a first body 50' and a second body 52'. First body 50' further includes a top surface 54', a bottom surface 56', a front face 58' and a rear face 60'. In addition, first body 50' defines a channel 62' extending from top surface 54' to bottom surface 56' near where first body 50' connects with second body 52'. A set screw 64' preferably extends through a threaded aperture 66' from front face 58' toward rear face 60', and into channel 62'. Rotation of set screw 64' in one direction or the other acts so as to move a portion of the screw into or out of channel 62'. First body 50' also includes one or more connection apertures 68' extending from front face 50' to rear face 60'. These apertures are preferably designed to receive pins or the like to facilitate a reinforcing connection of guide portion 14' to a bone, such as the tibia.

Second body 52' of second guide portion 14' is preferably connected to first body 50'. Second body 52' includes its own top surface 70' and bottom surface 72', and one or more connection apertures 74' extending through body 52' from the top to bottom surfaces. In addition, second body 52' includes a front face 76' and a rear face 78'. As with guide portion 12', second body 52' may be formed integrally with first body 50' through, for example a molding or milling process, or body 52' may be fixable attached to body 50' through the use of, for example, a welding or other well-known attachment process. Once again, in certain embodiments, it is possible for second body 52' to be moveable with respect to first body 50'.

However, rather than an element like intermediate portion 16 of guide 10, guide 10' exhibits a design in which first guide portion 12' is directly connected to second guide portion 14'. Preferably, one of apertures 74' of second guide portion 14' is capable of extending over and aligning with one of apertures 42' of first guide portion 12'. Thereafter, a connector 88' (similar in nature to locking knob 88 of guide 10) may be inserted through the aligned apertures to pivotally lock first and second guide portions 12' and 14' together. This connector also preferably allows for a navigation tracker (like those discussed above) to be attached to guide 10'. In fact, the particular connector design shown is the subject of commonly owned U.S. Patent Application Publication No. 2006/0089641, the disclosure of which is hereby incorporated by reference herein. It is to be understood that the outside aperture 74' of second guide portion 14' is essentially designed to lie over a thinned portion of second body 20'. However, additional apertures 74' could lie over similarly thinned sections, thereby facilitating the connection of second guide portion 14' to first guide portion 12' through different aligned apertures.

The use of guide 10' is essentially the same as that of guide 10. However, the mode of connecting first and second guide portions 12' and 14', without an intermediate portion, makes both truly pivotable with respect to only one another. In addition, FIGS. 11-13 depict a positioning arm 130' affixed to second guide portion 14'. This positioning arm may aid the surgeon or other medical professional in properly aligning guide 10' with respect to the bone to be resected. While only shown in connection with guide 10', it is to be understood that positioning arm 130' may be utilized in conjunction with guide 10.

Like with guide 10, each of the components of guide 10' are preferably constructed of material suitable for use in surgery (e.g., biocompatible materials), and also suitable for use with the cutting apparatus discussed below. In this regard, it is noted that the components should be made of a relatively hard and durable material, like stainless steel or the like. It is to be understood that the various components of guide 10 may vary from what is shown in the figures. For instance, the components of guide 10' may vary in their particular shape depending upon the particular bone being resected or the manner in which the guide is being utilized. All of these variations fall within the scope of the present invention. In addition, it is to be understood that certain different components may be employed in lieu of those shown. For example, instead of screws 32' and 64', another retaining means may be utilized, such as spring detents or the like. Likewise, each of the components of guide 10' may be manufactured in accordance with well-known processes, such as molding, milling or other processes often employed during the manufacture of medical devices and instruments.

Finally, it is noted that although both guides 10 and 10' have been discussed in relation to a method of performing a double uniconylar procedure, either guide may be similarly utilized in performing a traditional single unicondylar procedure. Obviously, such a procedure would only require a single incision and the guiding of a tool by either the first or second guide portions of either guide 10 or 10'. It is to be understood that guide 10 or 10' can be set up with both or just one of its first and/or second guide portions being attached to the one being utilized in guiding the cuts. Thus, a surgeon may only utilize a single guide portion in performing a single unicondylar procedure. Nonetheless, it is also possible to have both guide portions present in case it is determined, by the surgeon, that a double unicondylar procedure is required. In this regard, the initially unused guide portion could simply be pivoted out position during non-use and pivoted into position if needed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method of preparing a bone having first, second and third compartments comprising steps of:
providing a resection guide including a first resection guide portion including a first cutting surface and a second resection guide portion including a second cutting surface, the second resection guide portion being pivotally connected to the first resection guide portion;
positioning the first resection guide portion with respect to the first compartment of the bone;

rotating the second resection guide portion with respect to the first resection guide portion in order to position the second resection guide portion with respect to the second compartment of the bone;

resecting the first compartment by guiding a cutting instrument along the first cutting surface to create a first resected compartment;

resecting the second compartment by guiding a cutting instrument along the second cutting surface to create a second resected compartment;

implanting a first implant on the first resected compartment; and implanting a second implant on the second resected compartment, wherein the third compartment is not resected and the first and second implants are separate and not connected.

2. The method according to claim 1, further comprising the steps of fixing the first resection guide portion with respect to the first compartment and fixing the second resection guide portion with respect to the second compartment.

3. The method according to claim 2, wherein the fixing steps include inserting pins through the first and second resection guide portions.

4. The method according to claim 1, further comprising the step of fixing the first and second resection guide portions with respect to one another.

5. The method according to claim 4, wherein the step of fixing the first and second resection guide portions with respect to one another includes rotating a locking knob.

6. The method according to claim 1, further comprising the step of fixing the first resection guide portion to a leg extension.

7. The method according to claim 6, wherein the positioning step includes sliding a vertically extending rod of the leg extension through a first channel formed in the first resection guide portion and the fixing step includes fixing the vertically extending rod in the first channel.

8. The method according to claim 1, wherein the rotating step includes rotating the second resection guide portion with respect to an intermediate member attached to the first and second resection guide portions.

9. The method according to claim 1, wherein the resecting steps are performed with an oscillating tip saw.

10. The method according to claim 1, wherein the first compartment is a medial compartment of a tibia and the second compartment is a lateral compartment of the tibia.

11. The method according to claim 1, wherein the positioning the first resection guide portion with respect to a first compartment of the bone includes utilizing a navigation tracker.

12. A surgical method comprising steps of:
making an incision through skin adjacent a proximal end of a tibia;
providing a resection guide including a first resection guide portion including a first cutting surface and a second resection guide portion including a second cutting surface, the second resection guide portion being pivotally connected to the first resection guide portion;
positioning the first resection guide portion with respect to a lateral compartment of the tibia;
rotating the second resection guide portion with respect to the first resection guide portion in order to position the second resection guide portion with respect to a medial compartment of the tibia;
guiding an oscillating saw along the first cutting surface to resect the lateral compartment to create a lateral resected compartment;
guiding the oscillating saw along the second cutting surface to resect the medial compartment to create a medial resected compartment;
implanting a first implant on the lateral resected compartment; and
implanting a second implant on the medial resected compartment,
wherein a central compartment of the tibia is not resected and the first and second implants are separate and not connected.

13. The method according to claim 12, wherein the making step includes making a first incision adjacent the lateral compartment and making a second incision adjacent the medial compartment.

14. The method according to claim 12, further comprising the steps of fixing the first resection guide portion with respect to the lateral compartment and fixing the second resection guide portion with respect to the medial compartment.

15. The method according to claim 12, wherein the guiding steps include guiding an oscillating tip saw along the first and second cutting surfaces.

16. The method according to claim 12, wherein the first and second implants are unicondylar implants.

17. A surgical method comprising steps of:
making a first incision through skin adjacent a lateral compartment of a tibia;
making a second incision through skin adjacent a medial compartment of the tibia;
providing a resection guide including a first resection guide portion including a first cutting surface and a second resection guide portion including a second cutting surface, the second resection guide portion being pivotally connected to the first resection guide portion;
positioning the first resection guide portion with respect to the lateral compartment of the tibia;
rotating the second resection guide portion with respect to the first resection guide portion in order to position the second resection guide portion with respect to the medial compartment of the tibia;
fixing the first and second resection guide portions with respect to one another;
guiding an oscillating saw along the first cutting surface to create a resected lateral compartment;
guiding the oscillating saw along the second cutting surface to create a resected medial compartment;
implanting a first unicondylar implant on the resected lateral compartment; and
implanting a second unicondylar implant on the medial compartment,
wherein a central compartment of the tibia is not resected and the first and second implants are separate and not connected.

* * * * *